United States Patent
Singer

(10) Patent No.: US 8,645,163 B1
(45) Date of Patent: Feb. 4, 2014

(54) SYSTEMS AND METHODS FOR DETERMINING INFORMATION REGARDING DRUGS

(75) Inventor: Jonathan Lee Singer, Tenafly, NJ (US)

(73) Assignee: Jonathan Singer, Tenafly, NJ (US)

( * ) Notice: Subject to any disclaimer, the term of this patent is extended or adjusted under 35 U.S.C. 154(b) by 248 days.

(21) Appl. No.: 12/692,345

(22) Filed: Jan. 22, 2010

Related U.S. Application Data

(60) Provisional application No. 61/146,565, filed on Jan. 22, 2009.

(51) Int. Cl.
*G06Q 50/00* (2012.01)

(52) U.S. Cl.
USPC .................................. 705/3; 705/2; 705/4

(58) Field of Classification Search
USPC .......................................................... 705/2–4
See application file for complete search history.

(56) References Cited

U.S. PATENT DOCUMENTS

| | | | |
|---|---|---|---|
| 6,317,719 B1 | 11/2001 | Schrier et al. | |
| 7,505,917 B2 | 3/2009 | Howe et al. | |
| 7,574,370 B2 | 8/2009 | Mayaud | |
| 7,640,177 B2 | 12/2009 | Fralic | |
| 7,895,060 B1 * | 2/2011 | Mahoney et al. | 705/3 |
| 2002/0052760 A1 * | 5/2002 | Munoz et al. | 705/2 |
| 2002/0111832 A1 | 8/2002 | Judge | |
| 2003/0050799 A1 | 3/2003 | Jay et al. | |
| 2004/0039599 A1 | 2/2004 | Fralic | |
| 2004/0073457 A1 * | 4/2004 | Kalies | 705/2 |
| 2005/0149359 A1 | 7/2005 | Steinberg et al. | |
| 2005/0187793 A1 * | 8/2005 | Myles | 705/2 |
| 2005/0261939 A1 * | 11/2005 | Augspurger et al. | 705/2 |
| 2006/0149595 A1 | 7/2006 | Williams et al. | |
| 2006/0184391 A1 | 8/2006 | Barre et al. | |
| 2006/0265245 A1 * | 11/2006 | McCallie et al. | 705/2 |
| 2007/0043589 A1 | 2/2007 | Warren et al. | |
| 2007/0043595 A1 | 2/2007 | Pederson | |
| 2007/0162303 A1 | 7/2007 | Wiley, II et al. | |
| 2007/0226009 A1 | 9/2007 | Hicks | |
| 2007/0276697 A1 | 11/2007 | Wiley, II et al. | |
| 2008/0021736 A1 | 1/2008 | Elizabeth et al. | |
| 2009/0006141 A1 | 1/2009 | Karr | |

OTHER PUBLICATIONS

DestinationRx. "Compare Medicare Part D Plans." 2010 DestinationRx, Inc. http://plancompare.destinationrx.com/ Accessed on Feb. 19, 2010.

DestinationRx. "Compare Prices and Shop for Prescription Drugs." 2010 DestinationRx, Inc. http://www.destinationrx.com/ Accessed on Feb. 19, 2010.

(Continued)

*Primary Examiner* — Sind Phongsvirajati
(74) *Attorney, Agent, or Firm* — Carr & Ferrell LLP

(57) ABSTRACT

Systems, methods and media for determining information regarding drugs are provided herein. A healthcare plan identifier and a brand name drug identifier are received by a processor. Healthcare plan data and a formulary table associated with the healthcare plan data are obtained from one or more databases, based on the healthcare plan identifier. A drug tier associated with the brand name drug identifier is determined, based on the formulary table associated with the healthcare plan data, the healthcare plan data, and the brand name drug identifier. One or more costs associated with the brand name drug identifier is determined, based on the drug tier. Information regarding drugs is transmitted to display on a display.

33 Claims, 7 Drawing Sheets

(56) References Cited

OTHER PUBLICATIONS

Medicare.gov. "Medicare Prescription Drug Plan Finder." Centers for Medicare & Medicaid Services. U.S. Department of Health and Human Services. http://www.medicare.gov/MPDPF/Public/Include/DataSection/Questions. Accessed on Feb. 19, 2010.

Cigna Healthcare. "New myCIGNA.com Prescription Pricing Tool to Help Members Comparison Shop & Save." http://newsroom.cigna.com/article_print.cfm?article_id=681. Accessed on Feb. 19, 2010.

PharmacyChecker.com. "Find the best drug prices from verified online pharmacies." http://www.pharmacychecker.com. Accessed on Feb. 19, 2010.

PillBot.com. "Show me the best Price for the Prescription Medication . . . " http://www.pillbot.com/ Accessed on Feb. 19, 2010.

New York State Department of Health. "Prescription Drug Prices in New York State." http://rx.nyhealth.gov/pdpw/ Accessed on Feb. 19, 2010.

Bierbower, Elizabeth. "Engage! A Guide to Involving Your Consumers in Their Health." HCPro, Inc., 2007. http://www.hcmarketplace.com/prod-5783/Engage-A-Guide-to-Involving-Your-Consumers-in-Their-Health.html. Accessed on Feb. 22, 2010.

* cited by examiner

SYSTEMS AND METHODS FOR DETERMINING INFORMATION REGARDING DRUGS

CROSS-REFERENCE TO RELATED APPLICATIONS

This nonprovisional application claims the benefit and priority of U.S. Provisional Patent Application Ser. No. 61/146,565 filed on Jan. 22, 2009, titled "Prescription Price Comparison Service and Information Portal Available Online, Through Customer Service People and Using Handheld Electronic Devices," which is hereby incorporated by reference in its entirety.

FIELD OF THE INVENTION

This invention relates generally to systems and methods for determining information, and more particularly, to systems and methods for determining information regarding drugs.

SUMMARY OF THE INVENTION

Systems, methods and media for determining information regarding drugs are provided herein. One object of the present technology is to audit prescription usage of employers using data that is provided by health insurance companies. Another object of the present technology is to recommend prescription drug plan designs based on information regarding prescriptions to encourage the use of generic drugs. A further object of the present technology is to allow companies to provide healthcare drug plan information or drug plan information (including but not limited to co-payments and deductibles), thereby allowing employees of an employer to search drugs, generic equivalents, and view potential monthly and annual savings of buying generic drugs from major retailers or through buying by mail order.

These and other objects of the present technology are achieved in a method of determining information regarding drugs. A healthcare plan identifier and a brand name drug identifier are received by a processor. Healthcare plan data and a formulary table associated with the healthcare plan data are obtained from one or more databases, based on the healthcare plan identifier. A drug tier associated with the brand name drug identifier is determined, based on the formulary table associated with the healthcare plan data, the healthcare plan data, and the brand name drug identifier. One or more costs associated with the brand name drug identifier is determined, based on the drug tier. Information regarding drugs is transmitted to display on a display.

In some embodiments, the objects of the present technology may be implemented by executing a program by a processor, wherein the program may be embodied on a computer readable storage medium.

DETAILED DESCRIPTION OF THE INVENTION

Embodiments of the present invention provide systems, methods, and media for determining information regarding drugs. A prescription may be characterized as a set of instructions for governing the healthcare of a patient. A patient may obtain prescriptions from a health professional, who may participate in one or more healthcare networks and provide care to the patient in accordance with one or more healthcare plans. A patient may purchase a membership to a healthcare plan. Alternatively, the patient may be an employee of a company, and therefore may enroll in one or more employer-provided healthcare plans.

An employer may provide one or more healthcare plans to employees corresponding to one or more healthcare networks and/or healthcare plans. Healthcare plans may include a plurality of sub-plans, at least one of which provides guidelines and/or instructions as to the co-pay options and deductibles for prescription products. The present disclosure focuses on the dispensation of drugs, which includes, but is not limited to brand-name drugs, generic drugs, and retail generic drugs. However, it is contemplated that the disclosure provided herein may be applied to the dispensation of any products for which prescriptions from a health professional are required.

The systems, methods, and media presented herein allow for an employee covered by an employer-provided health plan to analyze prescription drug dispensation alternatives. Such analyses can be made by a program executable by a processor to determine co-pay comparisons and/or cost savings. In some embodiments, the program can be executed to compare brand-name drugs and corresponding generic drugs based on cost. Additionally, if retail generic drug alternatives are available, a cost comparison among the brand-name drugs, generic drugs, and retail generic drugs can be made. Once a cost comparison or analysis is made, a report (e.g., an employee report) may be furnished to an end-user (e.g., an employee or a patient) to provide them with the cost comparisons and savings. Other reports may also be provided, such as an employer report that provides an analysis of which type of healthcare plan works best for the employees of the employer, based on the drug cost comparisons using the methods described herein.

As used throughout this disclosure, the term "retail generic drug" is synonymous with the term "supersaver generic drug," and it refers to a subset of generic drugs which are provided by retail pharmacies to be purchased at a very low price (such as $4 per month or $10 for a 3-month supply). Such supersaver retail pharmacies that supply these retail generic drugs may identify the retail generic drugs on a list.

Figure 1:
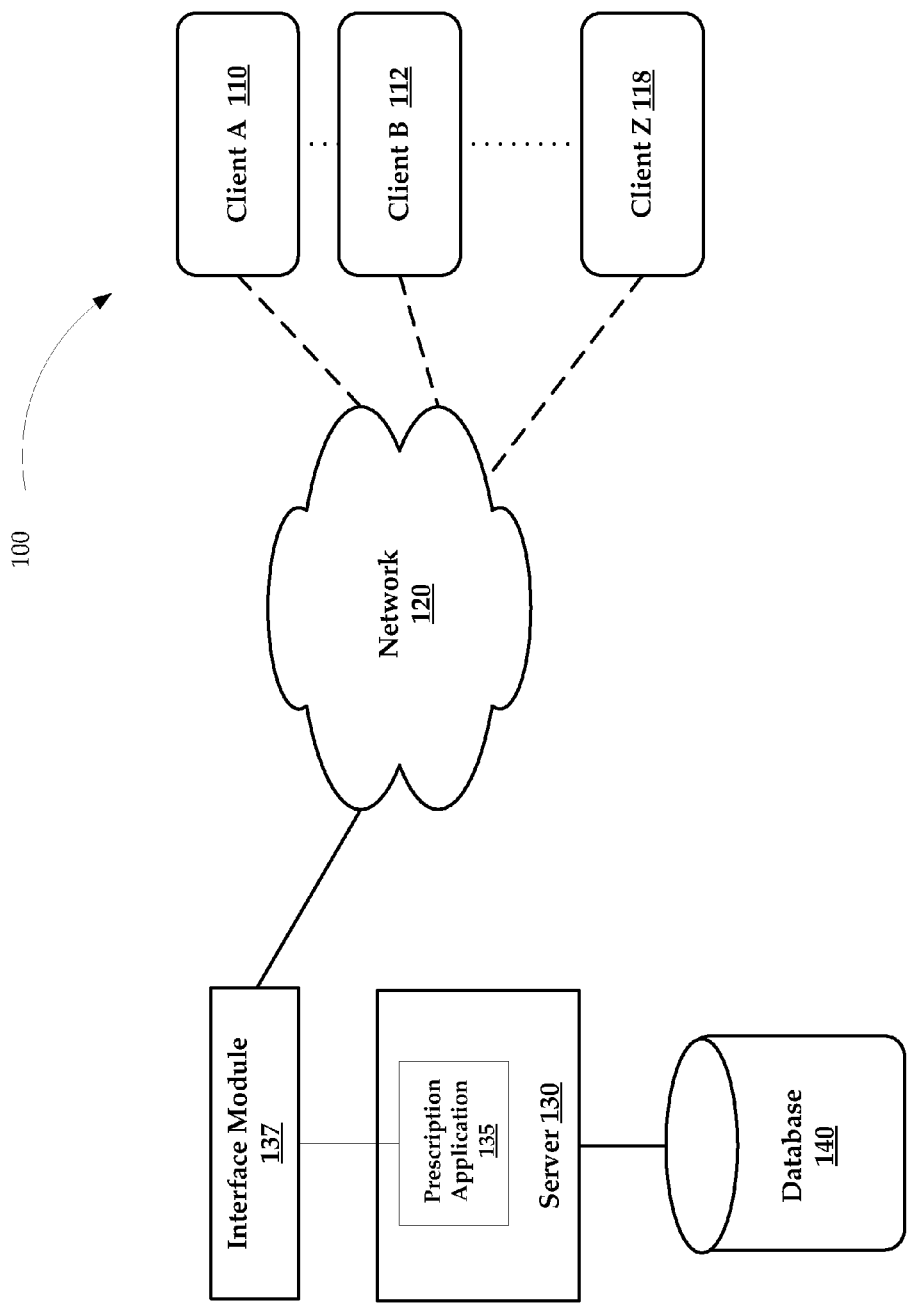
FIG. 1 is a block diagram of an exemplary networking environment in accordance with embodiments of the present invention.

FIG. 1 is a block diagram of an exemplary networking environment 100 in accordance with embodiments of the present invention. The networking environment 100 includes clients A 110, B 112, and so forth through client Z 118 (additional or fewer clients may be implemented), a network 120, a server 130 with a prescription application 135 and an interface module 137, and a database 140. As with all of the figures provided herein, one skilled in the art will recognize that any number of elements 110-140 can be present in the networking environment 100 and that the exemplary methods described herein can be executed by one or more of elements 110-140. Any number of any of elements 110-140 can be present in the networking environment 100, and the networking environment 100 is configured to serve these elements. For example, the server 130 may transmit a report via the network 120 to clients 110-118, despite the fact that only three clients are shown in FIG. 1. For all figures mentioned herein, like numbered elements refer to like elements throughout.

Clients 110-118 may be implemented as computers having a processor that runs software stored in memory, wherein the software may include network browser applications (not shown) configured to render content pages, such as web pages, from the server 130. Clients 110-118 can be any computing device, including, but not limited to desktop computers, laptop computers, mobile devices, and portable digital assistants (PDAs). The clients 110-118 can communicate with a web service provided by the server 130 over the network 120. Additionally, the clients 110-118 may be configured to store an executable application that encompasses one or more functionalities provided by the prescription application 135.

The network 120 can be any type of network, including but not limited to the Internet, LAN, WAN, a telephone network, and any other communication network that allows access to data, as well as any combination of these. The network 120 may be coupled to any of the clients 110-118, the interface module 137, and/or the server 130. As with all the figures provided herewith, the networking environment 100 is exemplary and not limited to what is shown in FIG. 1.

The server 130 can communicate with the network 120 and the database 140. It will be apparent to one skilled in the art that the embodiments of this invention are not limited to any particular type of server and/or database. For example, server 130 may include one or more application servers, one or more web servers, or a combination of such servers. In some embodiments, the servers mentioned herein are configured to control and route information via the network 120 or any other networks (additional networks not shown in FIG. 1). The servers herein may access, retrieve, store and otherwise process data stored on any of the databases mentioned herein.

Interface Module 137 may be implemented as a machine separate from server 130 or as hardware, software, or combination of hardware and software implemented on server 130. In some embodiments, Interface Module 137 may relay communications between prescription application 135 and Network 120.

The database 140 may be configured to store one or more tables of data which are accessible to the prescription application 135. In a non-exhaustive list, such tables may include information and/or identifiers relating to employers, drugs, drug brand names, drugs that an employer uses, an itemized list of drugs, healthcare providers, healthcare plans, networks, sub-plans, formulary tables, retail pharmacies, pharmacy generics, analysts, survey questions, survey responses, alert data, data regarding healthcare plans, data regarding advertisements, and data regarding coupons. The database 140 may include a database of FDA drugs, drug formulary lists from one or more healthcare plans or healthcare providers, and drug formulary lists from one or more retail pharmacies.

The clients 110-118 may interface with the prescription application 135 on server 130 via the network 120 and the interface module 137. The prescription application 135 may receive requests and/or data from the clients 110-118. The clients 110-118, may provide data for storage in the database 140, and therefore may be in communication with the database 140. Likewise, the prescription application 135 may access the database 140 based on one or more requests received from the clients 110-118. Further details as to the data communicated in the networking environment 100 are described more fully herein.

Figure 2:
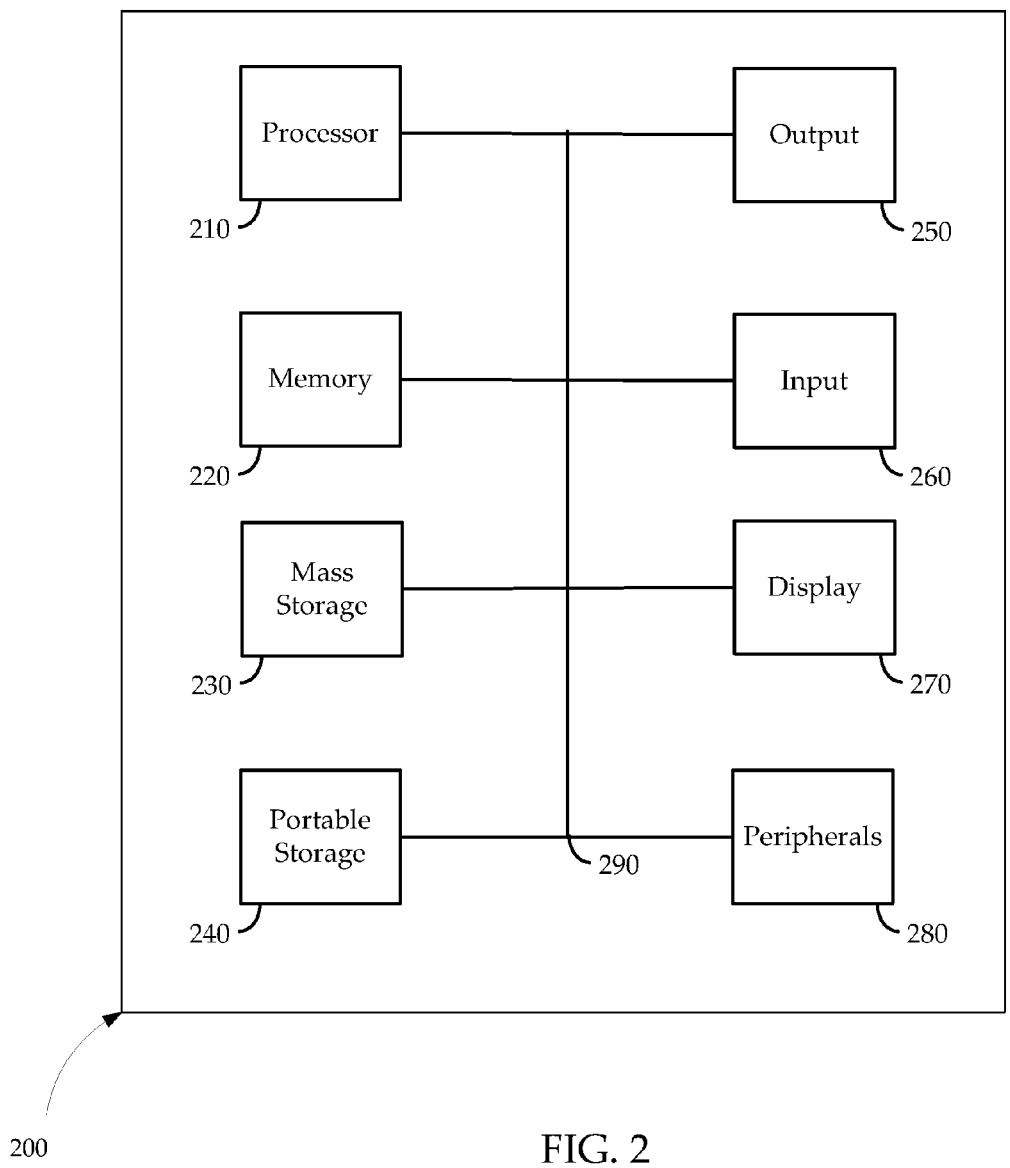
FIG. 2 is a block diagram of an exemplary computing device for determining information regarding drugs in accordance with embodiments of the present invention.

FIG. 2 is a block diagram of an exemplary computing device for determining information regarding drugs in accordance with embodiments of the present invention. In some embodiments, the exemplary computing device of FIG. 2 can be used to implement portions of the clients 110-118 and the server 130 as shown in FIG. 1.

The computing system 200 of FIG. 2 includes one or more processors 210 and memory 220. The main memory 220 stores, in part, instructions and data for execution by the processor 210. The main memory 220 can store the executable code when in operation. The system 200 of FIG. 2 further includes a mass storage device 230, portable storage 240 (which may be a storage or drive on any appropriate medium), output devices 250, user input devices 260, a display system 270, and peripheral devices 280.

The components illustrated in FIG. 2 are depicted as being connected via a single bus 290. However, the components can be connected through one or more data transport means. For example, the processor 210 and the main memory 220 can be connected via a local microprocessor bus, and the mass storage device 230, peripheral device(s) 280, the portable storage device 240, and the display system 270 can be connected via one or more input/output (I/O) buses.

The mass storage device 230, which can be implemented with a magnetic disk drive or an optical disk drive, is a non-volatile storage device for storing data and instructions for use by the processor 210. The mass storage device 230 can store the system software for implementing embodiments of the present invention for purposes of loading that software into the main memory 220.

The portable storage device 240 operates in conjunction with a portable non-volatile storage medium, such as a floppy disk, compact disk or digital video disc, to input and output data and code to and from the computer system 200 of FIG. 2. The system software for implementing embodiments of the present invention can be stored on such a portable medium and input to the computer system 200 via the portable storage device 240.

Input devices 260 provide a portion of a user interface. Input devices 260 may include an alpha-numeric keypad, such as a keyboard, for inputting alpha-numeric and other information, or a pointing device, such as a mouse, a trackball, stylus, or cursor direction keys. Additionally, the system 200 as shown in FIG. 2 includes output devices 250. Examples of suitable output devices include speakers, printers, network interfaces, and monitors.

The display system 270 may include a CRT, a liquid crystal display (LCD) or other suitable display device. Display system 270 receives textual and graphical information, and processes the information for output to the display device.

Peripherals 280 may include any type of computer support device to add additional functionality to the computer system. For example, peripheral device(s) 280 may include a modem or a router.

The components contained in the computer system 200 of FIG. 2 are those typically found in computer systems that can be suitable for use with embodiments of the present invention and are intended to represent a broad category of such computer components that are well known in the art. Thus, the computer system 200 of FIG. 2 can be a personal computer, hand held computing device, telephone, mobile computing device, workstation, server, minicomputer, mainframe computer, or any other computing device. The computer can also include various bus configurations, networked platforms, multi-processor platforms, etc. Various operating systems can be implemented, including Unix, Linux, Windows, Macintosh OS, Palm OS, and other suitable operating systems.

According to various embodiments, the computer system 200 may be preloaded with a list of available drugs on the market, a list of generic drugs available on the market and their brand name equivalents, one or more retail pharmacy's retail drug lists, an insurance company's formulary list, and a client or employer's drug plan providing which copayment applies to which tier for retail and mail order pharmacy orders.

Figure 3:
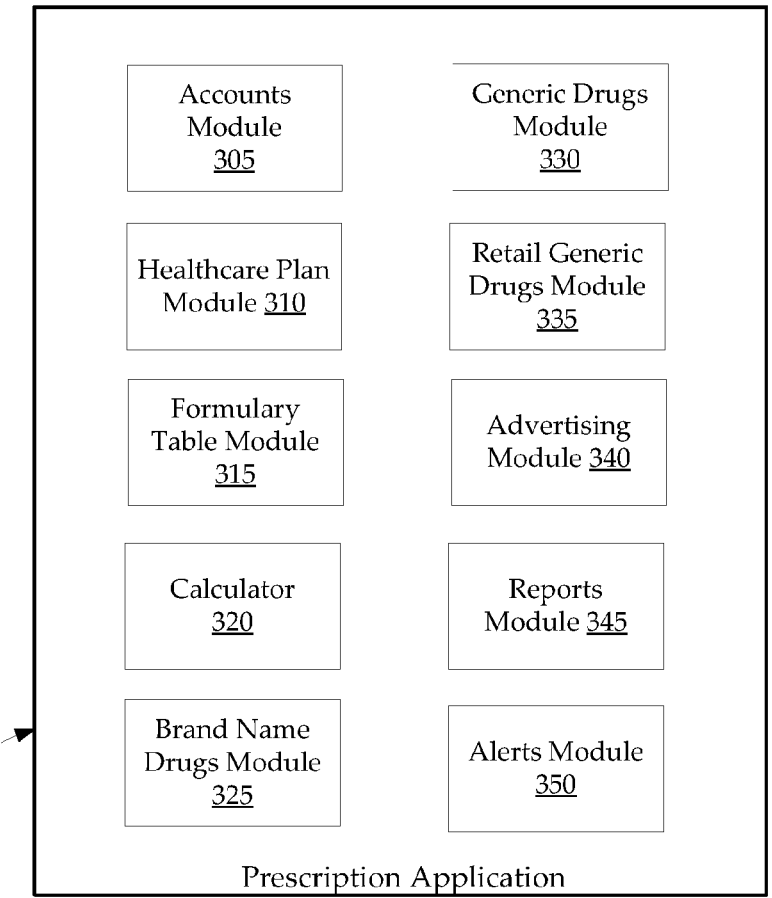
FIG. 3 is a block diagram of an exemplary architecture of a system for determining information regarding drugs.

FIG. 3 is a block diagram of an exemplary architecture of a system in the form of a prescription application 135 for determining information regarding drugs. Specifically, FIG. 3 as shown depicts further details of the prescription application 135, which is also shown as part of the networking environment 100 of FIG. 1. The prescription application 135 may include one or more modules for performing one or more methods as described herein. According to various embodiments of the present technology, the prescription application 135 includes an accounts module 305, a healthcare plan module 310, a formulary table module 315, a calculator 320, a brand name drugs module 325, a generic drugs module 330, a retail generic drugs module 335, an advertising module 340, a reports module 345, and an alerts module 350. Each of the modules 305-350 may communicate with one another. Although various modules may be configured to perform some or all of the various steps described herein, fewer or more modules may be provided and still fall within the scope of various embodiments.

The accounts module 305 is responsible for generating accounts, maintaining accounts, validating accounts for users on the system, and allowing access to accounts by users upon validation. The accounts module 305 may receive credentials by user input from a network-enabled device (such as clients A-Z 110-118 of FIG. 1) via an interface module (such as the interface module 137 of FIG. 1) regarding an account associated with a user identifier. The user identifier may be any identifier or identifying information associated with a user, such as user credentials, account number, account password, account login, pin number, one or more security questions, user contact information and any combination thereof.

The healthcare plan module 310 is configured for determining and storing data regarding healthcare plans. Healthcare plans may include sub-plans. The healthcare plan module 310 may store healthcare network plan identifiers and sub-plan identifiers. Determining healthcare plans may include determining healthcare plans and networks based on employee information provided by an employer. A non-exhaustive list of data regarding healthcare plans includes names and contact information of hospitals, doctors, healthcare providers, and other healthcare professionals that the healthcare plans cover, coverage details (including prescription drug coverage details), minimum and maximum coverage amounts, healthcare (copayment) costs for using in-network and out-of-network healthcare providers, copayment drug costs, deductibles, term of coverage, and the like.

The formulary table module 315 is configured for maintaining, storing and determining information from one or more drug formulary tables associated with one or more drugs. The drugs may include brand name drugs, mail by order drugs, retail generic (super saver) drugs, and generic drugs from pharmacies. The drug formulary tables or lists may be from a healthcare plan or provider or it may be a pharmacy.

The calculator 320 calculates cost savings and/or copayments associated with one or more drugs. Cost savings and/or copayments may be information relating to drugs that are provided in one or more reports, such as the employee report 600 in FIG. 6 and the employer report 710 in FIG. 7.

The brand name drugs module 325 is configured for identifying a brand name drug by a brand name drug identifier. The brand name drugs module 325 is further configured to maintain and store names of brand name drugs associated with user accounts for searches (past, present and/or future searches). Similarly, the generic drugs module 330 is configured for identifying a generic drug by a generic drug identifier. The generic drugs module 330 is further configured to maintain and store names of generic drugs associated with user accounts for searches (past, present and/or future searches). Similarly, the retail generic drugs module 335 is configured for identifying a retail generic drug by a generic drug identifier. The retail generic drugs module 335 is further configured to maintain and store names of retail generic drugs associated with user accounts for searches (past, present and/or future searches).

The advertising module 340 is configured for generating, providing and storing advertisements and/or coupons to the system and on reports for employees to print and bring to their doctors. Such advertisements and/or coupons will be related to the drug name entered by the employee or user, using the methods described herein, via a network-enabled device. The advertisement and/or coupons may be provided along with the exemplary employee report shown in FIG. 6. According to some embodiments, advertisements and/or coupons from retailers may be provided on the recommendation pages provided by the website, on any webpage online, and/or displayed on a handheld electronic device.

The reports module 345 is configured for generating, providing and storing reports. Exemplary reports for the employee and the employer are provided in FIGS. 6 and 7, respectively. The reports provide information relating to drugs using one or more methods described herein. For instance, the reports may provide the costs savings associated with purchasing a retail generic drug, rather than a brand name drug. The reports may also provide the costs savings associated with purchasing a retail generic drug from a retail store, rather than a brand name drug at a local pharmacy.

The alerts module 350 is configured for generating, providing and storing alerts based on costs and/or cost savings, and transmitting to display the alerts. An alert may be transmitted by an email or a text message. An option may be offered by the system to provide alerts via email or text messages to a display device with drug price updates on a weekly or monthly basis.

Figure 4:
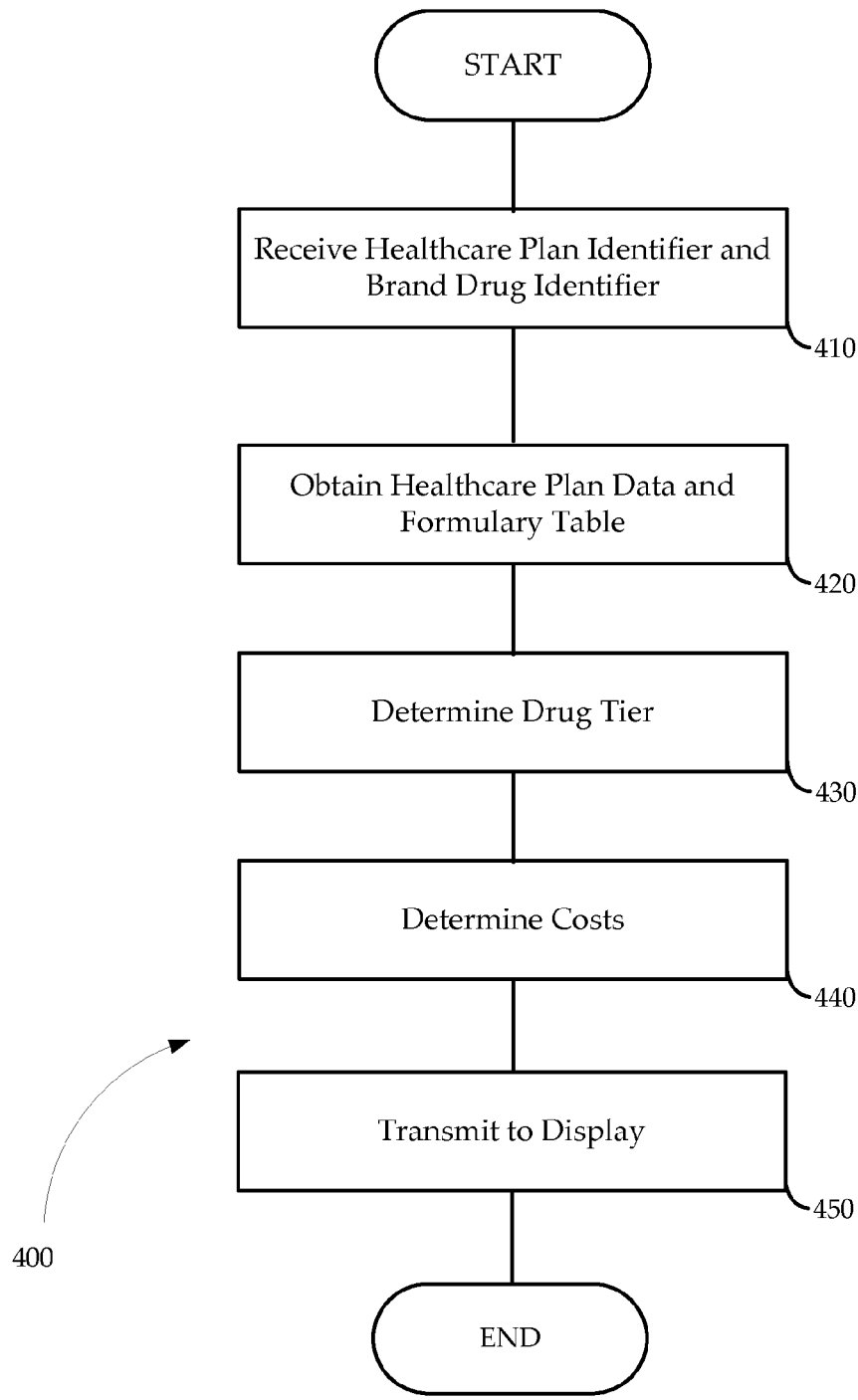
FIG. 4 is a flow diagram of an exemplary method for determining information regarding drugs.

FIG. 4 is a flow diagram of an exemplary method 400 for determining information regarding drugs. At step 410, a healthcare plan identifier and a brand name drug identifier are received. According to various embodiments, the healthcare plan identifier and the brand name drug identifier are received by user input via a network-enabled device (such as clients 110-118 in FIG. 1). A healthcare plan identifier may include the name or any other identifying information regarding the healthcare plan (such as an abbreviation or a plan number). The healthcare plan identifier may also include the healthcare network and the sub-plan. For instance, examples of the healthcare plan identifier include "Liberty $20 copay" (which provides the name of the healthcare plan and the dollar amount of the copayment) or "BlueCross BlueShield HMO 2400" (which provides the name of the healthcare plan, the dollar amount of the patient's annual deductible, and the subplan (e.g., HMO) identification.

At step 420, healthcare plan data and a formulary table associated with the healthcare plan data are obtained from one or more databases. The healthcare plan data and a formulary table may be retrieved from database 140 by prescription application 135 based on the obtained healthcare plan identifier. A non-exhaustive list of healthcare plan data include names, contact information and other data regarding healthcare providers, healthcare professionals, doctors, and hospitals which are covered by a given healthcare plan, costs, copayments, deductibles, data regarding formulary tables associated with a given healthcare plan, services, treatments and/or drugs covered by the healthcare plan, services, treatments and/or drugs not covered by the healthcare plan, and the like. A "formulary table associated with the healthcare plan data" is a list maintained by the healthcare plan (or insurance company that provides the healthcare plan), which supplies a drug (copayment) tier for each drug.

At step 430, a drug tier associated with the brand name drug identifier is determined, based on the formulary table associated with the healthcare plan data, the healthcare plan data, and the brand name drug identifier. In other words, the system may determine the drug tier that a brand name drug identifier falls under, based on the formulary table maintained by a given healthcare plan, data from the healthcare plan itself, and any identifying information associated with a brand name drug.

At step 440, one or more costs associated with the brand name drug identifier are determined, based on the drug tier. The costs may be coinsurance costs, copayments and/or deductibles. Finally, at step 450, information regarding drugs is transmitted to a display. The information regarding drugs may include the brand name drug identifier, the generic drug identifier, the drug tier, the one or more costs associated with the brand name drug identifier, a retail generic drug identifier, the identification of at least one retail pharmacy that supplies a given drug, the costs associated with mail order of the brand name drug identifier, the costs associated with mail order of the generic drug identifier, and the one or more costs associated with the retail generic drug identifier.

According to various embodiments of the present technology, the method 400 includes further optional steps (not shown). One or more retail generic drug identifiers may be obtained from the one or more databases, based on the brand name drug identifier. At least one retail pharmacy that carries one or more generic drugs is identified, based on the one or more retailer generic drug identifiers. One or more costs associated with the retail generic drug identifier are determined, based on a formulary table associated with the at least one retail pharmacy, the healthcare plan data, and the retail generic drug identifier. It should be noted that a "formulary table associated with at least one retail pharmacy" is similar to that of a "formulary table associated with healthcare plan data," in that a "formulary table associated with at least one retail pharmacy" is a list maintained by the retail pharmacy (not at healthcare plan or insurance company that provides the healthcare plan), where the list supplies a drug (copayment) tier for each drug. Further, it should be noted that the present technology allows for the information in databases (such as the database 140 of FIG. 1) to be updated, for example manually by a database administrator, based on the formulary tables provided by a healthcare plan website, a healthcare provider website and/or a retailer's website. The present technology also allows for the interfacing of the system with the FDA database (which provides brand name drugs and their generic equivalents) and one or more databases from one or more pharmacies, including supersaver pharmacies that provide a list of supersaver or retail generic drugs.

Further optional steps may be provided in the method 400. Costs associated with mail order of the brand name drug identifier may be determined, based on the formulary table associated with the healthcare plan data, the healthcare plan data, and the brand name drug identifier. Costs associated with mail order of the generic drug identifier may be determined, based on the formulary table associated with the healthcare plan data, the healthcare plan data, and the generic drug identifier. Copayments and costs savings associated with the brand name drug identifier may be determined. Information regarding drugs may be stored in one or more databases, such as the database 140 of FIG. 1.

Further optional steps of the method 400 include receiving credentials by user input by the processor regarding an account associated with a user identifier, validating credentials by the processor for a user to gain access to the account, based on the user identifier, and upon validation, providing access of the account to the user. These optional steps may be accomplished by an accounts module (such as the accounts module 305 of FIG. 3) of the prescription application 135 (FIGS. 1 and 3).

Yet further optional steps of the method 400 include generating an alert based on costs and transmitting to display the alert to the display. The alert may be transmitted by an email or a text message. These optional steps may be accomplished by an alerts module (such as the alerts module 350 of FIG. 3) of the prescription application 135 (FIGS. 1 and 3).

Yet further optional steps of the method 400 include adding a class for at least one of the brand name identifier, the retail generic drug identifier, and the generic drug identifier. The class may provide at least one unidentified brand name identifier, retail generic drug identifier, or generic drug identifier for treating a health condition. The health condition may be associated with the brand name identifier, the retail generic drug identifier, or the generic drug identifier. Another step may include transmitting for display the one unidentified brand name identifier, retail generic drug identifier, or generic drug identifier from the class.

The term "unidentified brand name identifier" refers to any identifier for a brand name drug that was not initially identified, inputted or otherwise supplied by a user of the system. For instance, an employee-user may input that he takes an antidepressant having a brand name identifier "X." These optional steps allow for the system to provide an unidentified (that is, unidentified by the user) brand name identifier that is within the class of the brand name identifier X. For example, the system may identify a brand name identifier "Y" which is within the same class as the brand name identifier X. According to some embodiments, the term "class" refers to a classification of drugs.

Referring back to the example, the brand name identifier "Y" (which was identified by the system) may belong to the same class (the classification of antidepressants or the classification of treating the same ailment of depression) as that of the brand name identifier "X" (which was provided by the employee-user). In some embodiments, the system may inform the user that although the brand name drug that is associated with the brand name identifier provided by the user is not available in a generic drug equivalent, there may be other drugs which do have generic drug equivalents and that can treat the same condition or ailment. The unidentified brand name identifiers may be stored in one or more databases coupled to the system.

Yet further optional steps of the method 400 include preloading into the system a cost of a drug at each pharmacy via a list of negotiated reimbursement fees for a plurality of retail pharmacies, determining which pharmacy has the lowest cost for the drug based on the list of negotiated reimbursement fees, and transmitting to display an identifier of the pharmacy providing the drug at the lowest cost based on the determination made. Insurance companies may negotiate a rate for each drug with a plurality of pharmacies on an individual basis. In other words, an insurance company may negotiate a first reimbursement rate for a drug with a first retail pharmacy and may negotiate a second reimbursement fee for the same drug with a second retail pharmacy. Where an end user pays a percentage of the cost of a drug (instead of a flat copayment), the system can identify to an end user which retail pharmacy they should visit to obtain the drug at the lowest cost based on the identified reimbursement fees that an insurance company has negotiated with two or more retail pharmacies.

For example, in the case where an employee pays 10% coinsurance, if the negotiated fee between an insurance company and a first pharmacy for a drug is $100, and the negotiated fee for the same drug with a second pharmacy is $120, the system determines that the employee must pay $10 at the first pharmacy or $12 at the second pharmacy for the given drug. The system then informs the employee that the lowest cost is provided if the employee buys the drug at the first pharmacy. It should be noted that data regarding the costs of a drug and the lists of negotiated reimbursement fees may be stored in a database (such as the database 140 of FIG. 1) or on a server (such as server 130 coupled with the prescription application 135 as depicted in FIG. 1).

System options that may require additional optional steps (not shown) to the method 400 include the following:

1. An option to print and/or email prescription search results to a doctor and/or to the user, with or without advertisements and/or coupons (which may be generated by the advertisement module 340 as depicted in FIG. 3.)
2. An option to search for drug information, such as side effects, warnings, and the like.
3. An option to search for wellness/prevention information and/or articles related to conditions that are being treated for by a given drug.
4. An option to save drug choices for future searches.
5. When searching for generic alternatives, an option for instant access to information regarding an online community regarding this system and/or community discussion groups about a) experiences using drugs, including side effects, b) effectiveness of generic drugs versus brand name drugs, c) health and wellness topics related to conditions treated by certain drugs, d) homeopathic remedy options and e) online discount offers/coupon codes at various retailers.
6. An option of accessing an online store, providing direct sales and/or web-links to online retailers for purchasing health and wellness-related items, such as books.
7. An option of an email, hotline and/or live chat during drug searches with pharmacists to seek answers to questions about drugs and generic alternatives.
8. An optional database of aggregated anonymous data relating to user searches and saved drug choices. Such a database may be made available to retailers, pharmaceutical companies and the like for press releases, whitepapers and/or to consumers or users of the system.

It should be noted that a user of the system may initially input or otherwise supply a brand name drug identifier, a generic drug identifier, or a retail generic identifier at the start of the method 400, and the system will still provide the information regarding drugs regardless of the initial input. Thus, if the user provides a generic drug identifier at the beginning of the method 400, the system may provide the brand name drug identifier and/or the retailer generic identifier that are associated with generic drug identifier. Further, one skilled in the art will recognize that the scope of the present technology allows for any order or sequence of the steps of the method 400 mentioned herein to be performed, and still provide the information regarding drugs that is sought.

Figure 5:
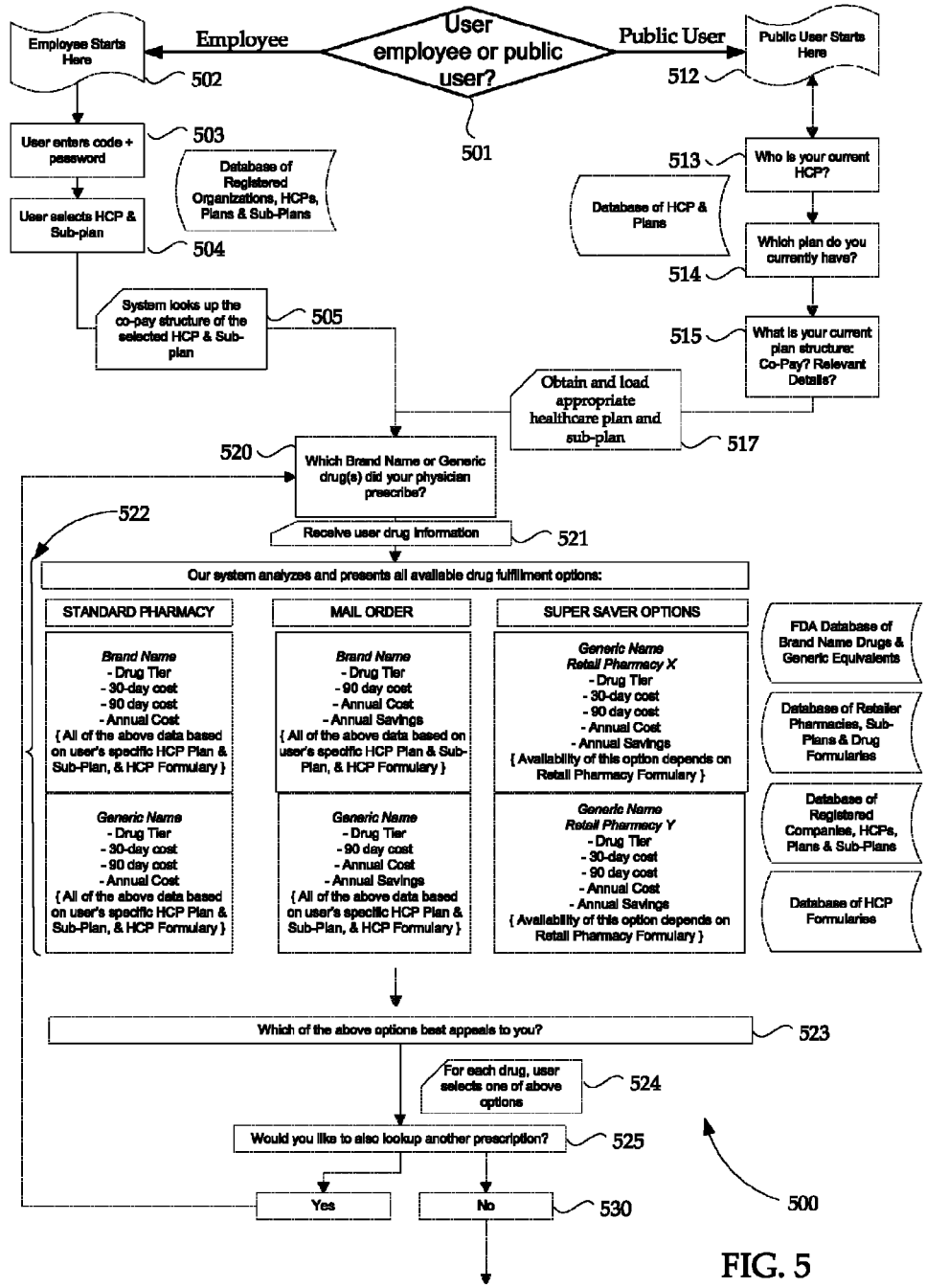
FIGS. 5 and 6 are flow diagrams of another exemplary method for determining information regarding drugs.
Figure 6:
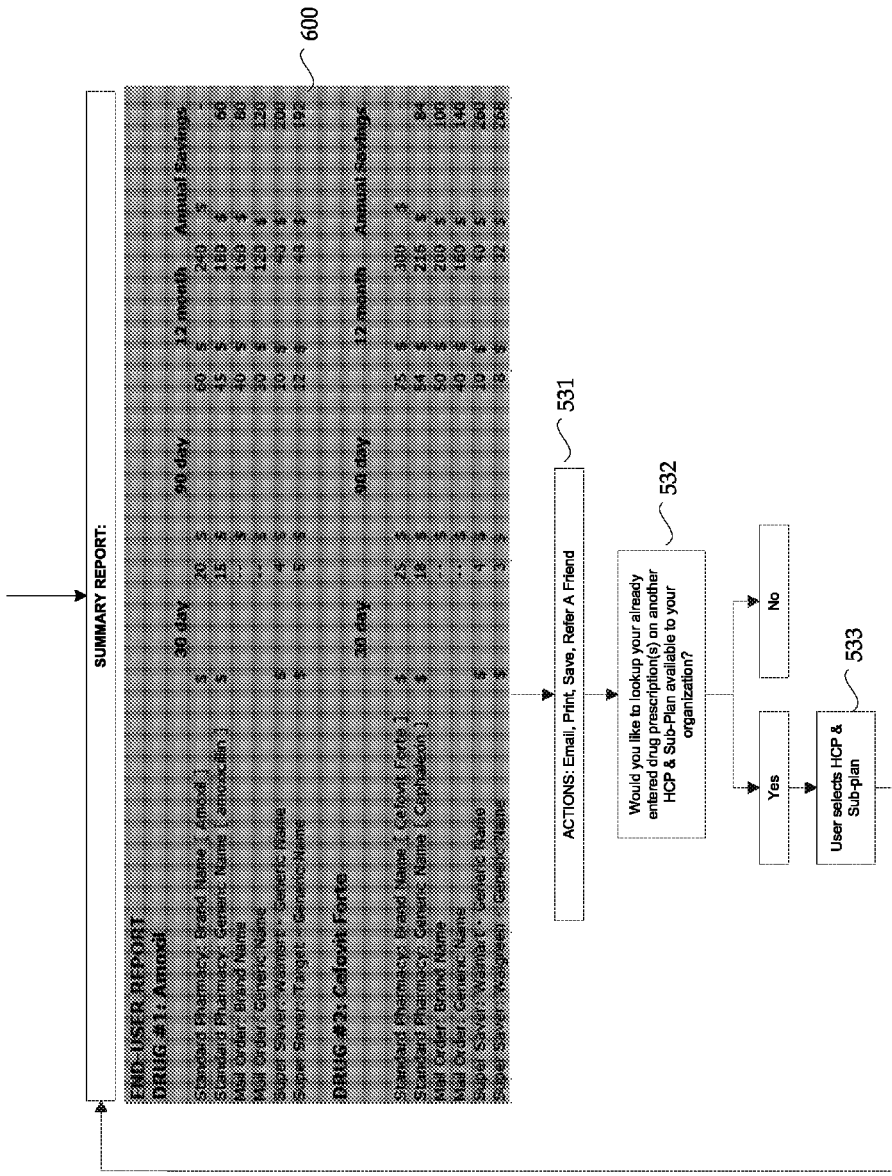

FIGS. 5 and 6 are flow diagrams of another exemplary method 500 for determining information regarding drugs. The method 500 begins with a determination 501 as to whether a user of the system is an employee of a company or a public user (that is, a user who is not an employee of a company but who is instead publicly accessing the system online).

If the user is an employee, then the method 500 continues at step 502, which is the starting point for an employee. If at the determination step 501 it is determined that the user is a public user, then the method 500 continues at step 512, which is the starting point for the public user.

Assuming that the user is an employee, at step 503, the employee enters a code and/or password. The code may be user credentials or an employee identifier. At step 504, the user selects a healthcare plan and a sub-plan which has been provided by the system. The system provides this information based on data in a database of registered organizations (namely, employers or other clients that have registered with the system), healthcare plans, healthcare providers and/or sub-plans. The healthcare plan and sub-plan selection may be provided to the user in any format, such as a drop-down menu selection, a radio button selection and the like. Once the user has selected the healthcare plan and the sub-plan, at step 505, the system retrieves the co-payment structure of the selected healthcare plan and sub-plan from the database of registered organizations, healthcare plans, healthcare providers and/or sub-plans.

If, on the other hand, the user is a public user, at step 513, the system displays the first of several questions for the public user to answer. At step 513, the system displays the question "Who is your current healthcare provider?" After receiving the answer from the public user to this question, at step 514, the system then displays to the public user the question of "Which [healthcare] plan do you currently have?" After receiving the answer from the public user to this question, at step 515, the system displays the questions "What is your current plan structure? Co-pay? Relevant Details?" Based on the answers obtained from the public user in steps 513-515, the system then can obtain and load the appropriate healthcare plan and sub-plan, for example from a database having healthcare providers, healthcare plans and/or sub-plans at step 517. At step 505, the system can also look up the co-pay structure of the selected healthcare plan and sub-plan.

At step 520, the system makes an inquiry of the user (the user being either an employee or a public user) of "Which brand name or generic drug(s) did your physician prescribe?" Once the user supplies this answer to the system at step 521, the system then analyzes and presents all available fulfillment options in step 522.

According to various embodiments of the present technology, at step 522, the system provides all available fulfillment options as information regarding drugs. The system may obtain information from a plurality of databases, including but not limited to the FDA database of brand name drugs and their drug equivalents, a database of retailer pharmacies, sub-plans and drug formularies (also known as formulary tables associated with a retail pharmacy), a database of registered companies, healthcare plans, healthcare providers and/or sub-plans, and a database of healthcare plan formularies (also known as formulary tables associated with healthcare plan data).

In the example provided in FIG. 5, the user indicated at step 521 that the drug prescribed to him or her was "Drug Z." For Drug Z, at step 522, the system may provide information relating to this drug, including the options of fulfilling the drug prescription at a standard pharmacy, through mail order and via a supersaver option. The system provides the information regarding Drug Z as depicted in FIG. 5. For instance, the system provides the drug tier, the 30-day cost, the 90-day cost, and the annual cost, all based on the user's specific healthcare plan, sub-plan and the formulary table associated with the healthcare plan data for fulfilling the prescription as a brand name drug or as a generic drug at a standard pharmacy. The system also provides information regarding Drug Z for the mail order option. Specifically, under the mail order option, the system provides the drug tier, the 90-day cost, and the annual savings, all based on the user's specific healthcare plan, sub-plan and the formulary table associated with the healthcare plan data for fulfilling the prescription as a brand name drug or as a generic drug via mail order. The system also provides information regarding Drug Z for the super saver (or retail generic) option. Specifically, under the super saver option, the system provides the drug tier, the 30-day cost, 90-day cost, the annual cost, and the annual savings, all based on the formulary table associated with a retail pharmacy for fulfilling the prescription as a retail generic drug. As depicted in FIG. 5, this information regarding retail generics may be provided based on information obtained from a plurality of retail pharmacies (such as Retail Pharmacy X and Retail Pharmacy Y). It may be that employees who buy retail generic drugs at retail pharmacies may do so without making an insurance claim, thereby allowing employers to reduce their prescription drug costs because fewer insurance claims would be submitted through their prescription drug plans.

At step 523, the system displays to the user the question of "Which of the above options best appeals to you?" At step 524, for each drug, the user selects one of the options. At step 525, the system displays to the user the question of "Would you like to also lookup another prescription?" If the user answers yes, then the system returns to step 520. If the user answers no to the question, then the method continues to FIG. 6, where a summary report is displayed to the user at step 530. An exemplary employee report 600 (also referred to as an end-user summary report) is shown in FIG. 6, which will be discussed in greater detail later herein.

Still referring to FIG. 6, after the user summary report is displayed to the user, the system provides options for the user to email, print, or save the summary report, or refer a friend at step 531. The user may select one or more of these options. After the selection is made, the system fulfills the user's request. At step 532, the system displays the question to the user of "Would you like to lookup your already entered drug prescription(s) on another healthcare plan and sub-plan available to your organization?" If the user selects yes, then the user can select another healthcare plan and sub-plan offered by the user's organization at step 533 and the system returns to step 530 to present the user with a summary report showing a summary of information regarding drugs based on the healthcare plan and sub-plan that the user has selected. If the user answers 'no' to the question presented in step 532, then the method 500 ends.

Now returning to the exemplary employee report 600 depicted in FIG. 6, it should be noted that the end-user report shows information relating to two drugs, namely Amoxil and Cefovit Forte. As with any report generated by the systems described herein, any number of drugs may be described in the employee report 600. Further, the employee report 600 provides the 30-day cost, the 90-day cost, the 12 month (or annual) cost, and the annual savings for each of the drugs listed. For drug #1, Amoxil, the employee report 600 shows that details for using the option of "Standard Pharmacy: Brand Name [Amoxil]." Specifically, the end-user report shows that under this option, the 30-day cost for having a standard pharmacy fulfill the prescription with supplying the brand name drug Amoxil is $20, the 90-day cost is $60, the 12 month (annual) cost is $240, and that there are no annual savings associated with this option.

In contrast, as shown in the employee report 600, the highest savings ($200) is projected to be through the option of "Super Saver: Walmart-Generic Name." In other words, if a user wants to save the most money, the user may do so by picking the option of "Super Saver: Walmart-Generic Name," which means that the user can fulfill the prescription at a super saver retail pharmacy (namely Walmart) with a retail generic drug. The highest savings provided by the option of "Super Saver: Walmart-Generic Name" is determined by subtracting $40 (which is the 12-month or annual cost for this option) from the 12-month or annual cost of $240 for exercising the option of "Standard Pharmacy: Brand Name [Amoxil]." Similar information and calculations for Drug #2 Cefovit Forte are also provided in the employee report 600.

Figure 7:
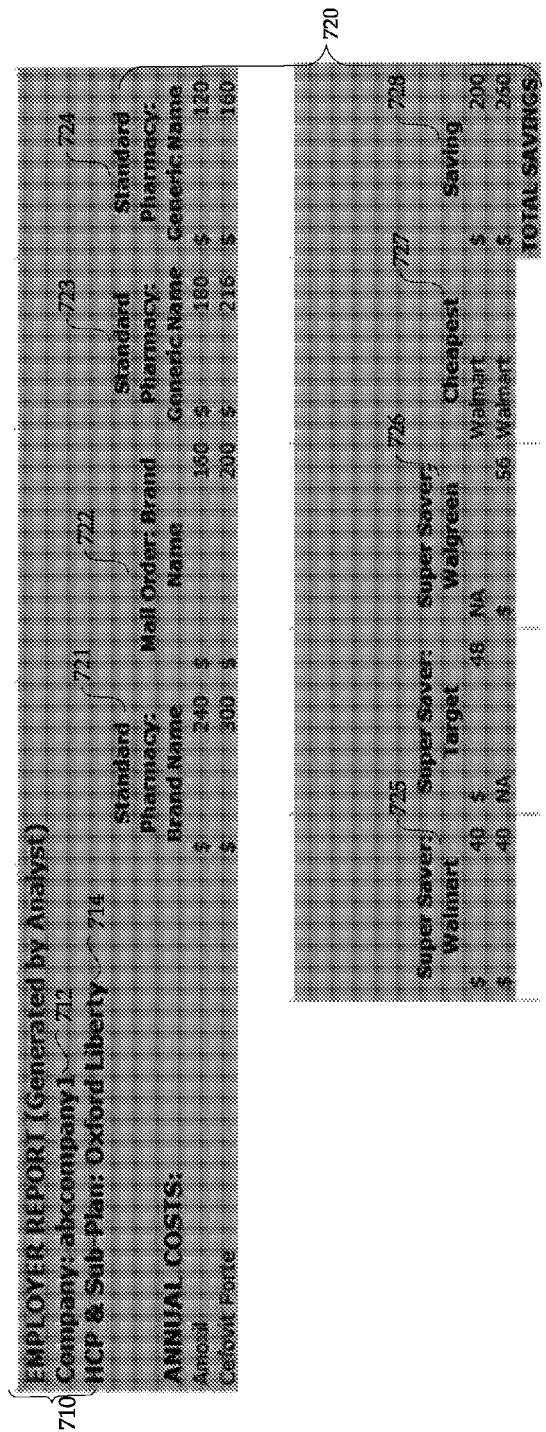
FIG. 7 is an exemplary screenshot of information relating to drugs displayed on a display on a network-enabled device interacting with an exemplary system of the technology described herein.

FIG. 7 is an exemplary screenshot 700 of information regarding drugs displayed on a display on a network-enabled device (such as clients A-Z 110-118 in FIG. 1) interacting with an exemplary system of the technology described herein. In some embodiments, screenshot 700 displays a portion of an interface, such as a web page interface, that may be provided to a user over network 120 by prescription application 135 through interface module 137. The exemplary screenshot 700 shows an employer report that provides information regarding drugs. In some embodiments, the employer report is generated by an analyst using the systems described herein based on the information that has been supplied or otherwise inputted by employee end-users. In the exemplary screenshot 700, the employer report 710 includes a company identifier 712 and the healthcare plan identifier 714. The company identifier 712 in the example shown in FIG. 7 shows that the employer report is for a company called named "abccompany1." The healthcare plan identifier 714 shows that the healthcare plan and sub-plan is called the "Oxford Liberty."

The screenshot 700 further shows the information regarding drugs obtained through one or more of the methods of the present technology described herein. Specifically, the body 720 of the screenshot 700 shows the annual costs for drugs. In the example provided in FIG. 7, the drugs that were supplied or inputted by the employee end-users were Amoxil and Cefovit Forte. The body 720 shows that the annual cost savings for Amoxil is $200 and the annual cost savings for Cefovit Forte. The body 720 further shows the information regarding drugs, including columns supplying the standard pharmacy costs for a brand name drug 721, the mail order costs for a brand name drug 722, the standard pharmacy costs for a generic drug for pharmacy A 723, the standard pharmacy costs for a generic drug supplied by pharmacy B 724, the super saver costs (or retail generic costs) for a retail store A (e.g., Walmart) 725, the super saver costs for a retail store B (e.g., Walgreen) 726, the identification of the cheapest supplier for a drug 727, and the total cost savings 728 for the drug determined by the system.

Still referring to FIG. 7, the cheapest supplier for Amoxcil Amoxil is Walmart. The system compares the standard pharmacy costs for a brand name drug 721, the mail order costs for a brand name drug 722, the standard pharmacy costs for a generic drug for pharmacy A 723, the standard pharmacy costs for a generic drug supplied by pharmacy B 724, the super saver costs (or retail generic costs) for a retail store A (e.g., Walmart) 725, and the super saver costs for a retail store B (e.g., Walgreen) 726. Walmart supplies a retail generic/super saver equivalent of the drug at the cheapest rate of $40. The most expensive supplier of the drug is provided in the column for standard pharmacy costs for a brand name drug 721, which shows that Amoxil is priced at $240. Thus, subtracting the cheapest costs ($40) from the expensive costs ($240) for Amoxil, it is determined that the total savings is $200, which is reflected in the column showing total cost savings for the drug 728 determined by the system. Similarly, Cefovit Forte is shown as to have a total cost savings of $260, if a patient purchases a retail generic/super saver equivalent of the drug from Walgreen at $40, as opposed to purchasing the brand name drug from a standard pharmacy for $300.

According to various embodiments, analysts may input or otherwise upload to the system lists of clients (e.g., employers and/or businesses), the healthcare plans currently provided by clients, credentials that clients can enter to take surveys, formulary tables in any format (including but not limited to PDF format which may be imported through spreadsheets), importing super-saving formulary tables through spreadsheets. Analysts may also provide, via the system, company-wide reports (such as the employer report 710 in FIG. 7), showing all the drugs that the employees of a company are interested in purchasing, the different options available to procure such drugs, and the dollar savings the company may enjoy if they pursue the most cost-effective option in comparison to the most expensive option as identified by the system.

Some of the above-described functions may be composed of instructions that are stored on storage media (e.g., computer-readable medium). The instructions may be retrieved and executed by the processor (such as the processor 210 in FIG. 2). Some examples of storage media are memory devices, tapes, disks, and the like. The instructions are operational when executed by the processor 210 to direct the processor 210 to operate in accord with the invention. Those skilled in the art are familiar with instructions, processor(s), and storage media.

It is noteworthy that any hardware platform suitable for performing the processing described herein is suitable for use with the invention. The terms "computer-readable storage medium" and "computer-readable storage media" as used herein refer to any medium or media that participate in providing instructions to a CPU for execution. Such media can take many forms, including, but not limited to, non-volatile media, volatile media and transmission media. Non-volatile media include, for example, optical or magnetic disks, such as a fixed disk. Volatile media include dynamic memory, such as system RAM. Transmission media include coaxial cables, copper wire and fiber optics, among others, including the wires that comprise one embodiment of a bus. Transmission media can also take the form of acoustic or light waves, such as those generated during radio frequency (RF) and infrared (IR) data communications. Common forms of computer-readable media include, for example, a floppy disk, a flexible disk, a hard disk, magnetic tape, any other magnetic medium, a CD-ROM disk, digital video disk (DVD), any other optical medium, punch cards, paper tape, any other physical medium with patterns of marks or holes, a RAM, a PROM, an EPROM, an EEPROM, a FLASHEPROM, any other memory chip or cartridge, a carrier wave, or any other medium from which a computer can read.

Various forms of computer-readable media may be involved in carrying one or more sequences of one or more instructions to a CPU for execution. A bus carries the data to system RAM, from which a CPU retrieves and executes the instructions. The instructions received by system RAM can optionally be stored on a fixed disk either before or after execution by a CPU.

The above description is illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents.

While the present invention has been described in connection with a series of preferred embodiment, these descriptions are not intended to limit the scope of the invention to the particular forms set forth herein. It will be further understood that the methods of the invention are not necessarily limited to the discrete steps or the order of the steps described. To the contrary, the present descriptions are intended to cover such alternatives, modifications, and equivalents as may be included within the spirit and scope of the invention as defined by the appended claims and otherwise appreciated by one of ordinary skill in the art.

What is claimed is:

1. A method for determining information regarding drugs, comprising:
receiving a healthcare plan identifier and a brand name drug identifier;
obtaining healthcare plan data and a formulary table associated with the healthcare plan data from one or more databases, based on the healthcare plan identifier;
determining by a processor executing instructions stored in memory a drug tier associated with the brand name drug identifier, based on the formulary table associated with the healthcare plan data, the healthcare plan data, and the brand name drug identifier;
determining one or more costs associated with the brand name drug identifier, based on the drug tier and a pharmacy, the pharmacy offering a lowest cost associated with the brand name drug identifier;
retrieving anonymous data relating to user searches and saved drug choices;
aggregating the anonymous data relating to the user searches and the saved drug choices; and
transmitting information regarding drugs to a display, the information regarding drugs including the brand name drug identifier, the drug tier, an advertisement related to the brand name drug identifier, and the one or more costs associated with the brand name drug identifier.

2. The method of claim 1, further comprising:
obtaining one or more retail generic drug identifiers from the one or more databases, based on the brand name drug identifier;
identifying at least one retail pharmacy that carries one or more generic drugs, based on the one or more retail generic drug identifiers;
determining one or more costs associated with the retail generic drug identifier, based on a formulary table associated with the at least one retail pharmacy, the healthcare plan data, and the retail generic drug identifier; and
transmitting information regarding drugs to the display, the information regarding drugs including the retail generic drug identifier, the identification of at least one retail pharmacy, a coupon related to the retail generic drug identifier, and the one or more costs associated with the retail generic drug identifier.

3. The method of claim 2, further comprising:
determining costs associated with mail order of the brand name drug identifier, based on the formulary table associated with the healthcare plan data, the healthcare plan data, and the brand name drug identifier; and
determining costs associated with mail order of the generic drug identifier, based on the formulary table associated with the healthcare plan data, the healthcare plan data, and the generic drug identifier; and
transmitting information regarding drugs to the display, the information regarding drugs including the brand name drug identifier, the generic drug identifier, the drug tier, the costs associated with mail order of the brand name drug identifier, and the costs associated with mail order of the generic drug identifier.

4. The method of claim 1, wherein determining one or more costs associated with the brand name drug identifier further comprises calculating copayments and costs savings associated with the brand name drug identifier, and wherein the healthcare plan includes a healthcare plan network identifier and a sub-plan identifier.

5. The method of claim 1, further comprising:
receiving credentials by user input regarding an account associated with a user identifier;
validating credentials for a user to gain access to the account, based on the user identifier; and
upon validation, providing access of the account to the user.

6. The method of claim 1, further comprising:
generating an alert based on costs; and
transmitting to display the alert to the display.

7. The method of claim 6, wherein the alert is transmitted by an email or a text message.

8. The method of claim 1, further comprising:
storing in a database the information regarding drugs.

9. The method of claim 1, further comprising:
adding a class for at least one of the brand name identifier, the retail generic drug identifier, and the generic drug identifier, the class providing at least one unidentified brand name identifier, retail generic drug identifier, or generic drug identifier for treating a health condition that is associated with the brand name identifier, the retail generic drug identifier, or the generic drug identifier; and
transmitting to display to the display the one unidentified brand name identifier, retail generic drug identifier, or generic drug identifier from the class.

10. The method of claim 1, further comprising:
preloading a cost of a drug for each of a plurality of pharmacies, based on a list of negotiated reimbursement fees;
determining which pharmacy from the plurality of pharmacies has a lowest cost for the drug, based on a comparison of negotiated reimbursement fees charged by the plurality of pharmacies, as provided in the list of negotiated reimbursement fees; and
transmitting an identifier of the pharmacy that provides drug at the lowest cost based on the determination made.

11. The method of claim 1, wherein the pharmacy is determined to supply the brand name drug identifier.

12. The method of claim 1, further comprising:
determining that the brand name drug identifier is not associated with a generic drug; and
recommending a second brand name drug identifier that is associated with a generic drug.

13. A non-transitory computer readable storage medium having embodied thereon a program, the program being executable by a processor to perform a method for determining information regarding drugs, the method comprising:
receiving a healthcare plan identifier and a brand name drug identifier;
obtaining healthcare plan data and a formulary table associated with the healthcare plan data from one or more databases, based on the healthcare plan identifier;
obtaining one or more retail generic drug identifiers from the one or more databases, based on the brand name drug identifier;
identifying at least one retail pharmacy that carries one or more generic drugs, based on the one or more retailer generic drug identifiers;
determining by the processor executing instructions stored in memory a drug tier associated with the brand name drug identifier, based on the formulary table associated with the healthcare plan data, the healthcare plan data, and the brand name drug identifier;
determining one or more costs associated with the brand name drug identifier, based on the drug tier and a pharmacy, the pharmacy offering a lowest cost associated with the brand name drug identifier;
determining one or more costs associated with the retail generic drug identifier, based on a formulary table associated with the at least one retail pharmacy, the healthcare plan data, and the retail generic drug identifier;
retrieving anonymous data relating to user searches and saved drug choices;
aggregating the anonymous data relating to the user searches and the saved drug choices; and
transmitting information regarding drugs to a display, the information regarding drugs including the brand name drug identifier, the retail generic drug identifier, the identification of at least one retail pharmacy, the drug tier, the one or more costs associated with the brand name drug identifier, an advertisement related to the brand name drug identifier, and the one or more costs associated with the retail generic drug identifier.

14. The computer readable storage medium of claim 13, the method further comprising:
determining costs associated with mail order of the brand name drug identifier, based on the formulary table associated with the healthcare plan data, the healthcare plan data, and the brand name drug identifier; and
determining costs associated with mail order of the generic drug identifier, based on the formulary table associated with the healthcare plan data, the healthcare plan data, and the generic drug identifier; and
transmitting information regarding drugs to the display, the information regarding drugs including the brand name drug identifier, the generic drug identifier, the costs associated with mail order of the brand name drug identifier, a coupon related to the retail generic drug identifier, and the costs associated with mail order of the generic drug identifier.

15. The computer readable storage medium of claim 13, wherein determining one or more costs associated with the brand name drug identifier further comprises calculating copayments and costs savings associated with the brand name drug identifier, and wherein the healthcare plan includes a healthcare plan network identifier and a sub-plan identifier.

16. The computer readable storage medium of claim 13, the method further comprising:
receiving credentials by user input regarding an account associated with a user identifier;

validating credentials for a user to gain access to the account, based on the user identifier; and upon validation, providing access of the account to the user.

17. The computer readable storage medium of claim 13, the method further comprising:

generating an alert based on costs; and transmitting to display the alert to the display.

18. The computer readable storage medium of claim 13, wherein the alert is transmitted by an email or a text message.

19. The computer readable storage medium of claim 13, the method further comprising:

storing in a database the information regarding drugs.

20. The computer readable storage medium of claim 13, the method further comprising:

preloading a cost of a drug for each of a plurality of pharmacies, based on a list of negotiated reimbursement fees;

determining which pharmacy from the plurality of pharmacies has a lowest cost for the drug, based on a comparison of negotiated reimbursement fees charged by the plurality of pharmacies, as provided in the list of negotiated reimbursement fees; and transmitting to the display an identifier of the pharmacy that provides drug at the lowest cost based on the determination made.

21. The computer readable storage medium of claim 13, wherein the pharmacy is determined to supply the brand name drug identifier.

22. The computer readable storage medium of claim 13, the method further comprising:

determining that the brand name drug identifier is not associated with a generic drug; and recommending a second brand name drug identifier that is associated with a generic drug.

23. A system for determining information regarding drugs, the system comprising:

a memory configured to store information;

a processor configured for executing instructions stored in memory to:

receive a healthcare plan identifier and a brand name drug identifier;

obtain healthcare plan data and a formulary table associated with the healthcare plan data from one or more databases, based on the healthcare plan identifier;

obtain one or more retail generic drug identifiers from the one or more databases, based on the brand name drug identifier;

identify at least one retail pharmacy that carries one or more generic drugs, based on the one or more retail generic drug identifiers;

determine a drug tier associated with the brand name drug identifier, based on the formulary table associated with the healthcare plan data, the healthcare plan data, and the brand name drug identifier;

determine one or more costs associated with the brand name drug identifier, based on the drug tier and a pharmacy, the pharmacy offering a lowest cost associated with the brand name drug identifier;

retrieve anonymous data relating to user searches and saved drug choices;

aggregate the anonymous data relating to the user searches and the saved drug choices; and determine one or more costs associated with the retail generic drug identifier, based on a formulary table associated with the at least one retail pharmacy, the healthcare plan data, and the retail generic drug identifier; and an interface configured to transmit to display information regarding drugs to a display, the information regarding drugs including the brand name drug identifier, the retail generic drug identifier, the identification of at least one retail pharmacy, the drug tier, the one or more costs associated with the brand name drug identifier, an advertisement related to the brand name drug identifier, and the one or more costs associated with the retail generic drug identifier.

24. The system of claim 23, wherein the processor is further configured for executing instructions stored in memory to:

determine costs associated with mail order of the brand name drug identifier, based on the formulary table associated with the healthcare plan data, the healthcare plan data, and the brand name drug identifier; and determine costs associated with mail order of the generic drug identifier, based on the formulary table associated with the healthcare plan data, the healthcare plan data, and the generic drug identifier; and wherein the interface is further configured to transmit the generic drug identifier, the costs associated with mail order of the brand name drug identifier, a coupon related to the retail generic drug identifier, and the costs associated with mail order of the generic drug identifier to the display.

25. The system of claim 23, wherein determining one or more costs associated with the brand name drug identifier further comprises calculating copayments and costs savings associated with the brand name drug identifier, and wherein the healthcare plan includes a healthcare plan network identifier and a sub-plan identifier.

26. The system of claim 23, wherein the processor is further configured for executing instructions stored in memory to:

generate an alert based on costs; and transmit the alert to the display.

27. The system of claim 23, further comprising:

a database configured for storing the information regarding drugs.

28. The system of claim 23, wherein the processor is further configured for executing instructions stored in memory to:

preload a cost of a drug for each of a plurality of pharmacies, based on a list of negotiated reimbursement fees;

determine which pharmacy from the plurality of pharmacies has a lowest cost for the drug, based on a comparison of negotiated reimbursement fees charged by the plurality of pharmacies, as provided in the list of negotiated reimbursement fees; and transmit to the display an identifier of the pharmacy that provides drug at the lowest cost based on the determination made.

29. The system of claim 23, wherein the pharmacy is determined to supply the brand name drug identifier.

30. The system of claim 23, the processor further configured for executing instructions stored in memory to:

determine that the brand name drug identifier is not associated with a generic drug; and recommend a second brand name drug identifier that is associated with a generic drug.

31. A method for determining information regarding drugs, comprising:
- receiving a healthcare plan identifier and a brand name drug identifier;
- obtaining healthcare plan data and a formulary table associated with the healthcare plan data from one or more databases, based on the healthcare plan identifier;
- determining by a processor executing instructions stored in memory a drug tier associated with the brand name drug identifier, based on the formulary table associated with the healthcare plan data, the healthcare plan data, and the brand name drug identifier;
- determining one or more costs associated with the brand name drug identifier, based on the drug tier and a pharmacy, the pharmacy offering a lowest cost associated with the brand name drug identifier;
- determining which pharmacy from the plurality of pharmacies has a lowest cost associated with the brand name drug identifier, based on a comparison of negotiated reimbursement fees charged by the plurality of pharmacies, as provided in the list of negotiated reimbursement fees;
- retrieving anonymous data relating to user searches and saved drug choices;
- aggregating the anonymous data relating to the user searches and the saved drug choices; and
- transmitting information regarding drugs to a display, the information regarding drugs including the brand name drug identifier, the drug tier, the one or more costs associated with the brand name drug identifier, an advertisement related to the brand name drug identifier, and an identifier of the pharmacy that provides drug at the lowest cost.

32. The method of claim 31, wherein:
- the pharmacy is determined to supply the brand name drug identifier; and
- the advertisement includes a coupon related to the retail generic drug identifier.

33. The method of claim 31, further comprising:
- determining that the brand name drug identifier is not associated with a generic drug; and
- recommending a second brand name drug identifier that is associated with a generic drug.

* * * * *